(12) United States Patent
Maples (10) Patent No.: US 10,136,851 B2
(45) Date of Patent: Nov. 27, 2018

(54) INTEGRATED DEVICE TO MEASURE VARIATIONS IN NEUROMUSCULAR CONTROL WHEN TRACING DEFINED TARGET PATTERNS AND A SYSTEM AND METHOD OF USING THE INTEGRATED DEVICE

(71) Applicant: John A. Maples, Miami Shores, FL (US)

(72) Inventor: John A. Maples, Miami Shores, FL (US)

(*) Notice: Subject to any disclaimer, the term of this patent is extended or adjusted under 35 U.S.C. 154(b) by 185 days.

(21) Appl. No.: 15/204,358

(22) Filed: Jul. 7, 2016

(65) Prior Publication Data

US 2017/0055886 A1    Mar. 2, 2017

Related U.S. Application Data

(60) Provisional application No. 62/213,164, filed on Sep. 2, 2015.

(51) Int. Cl.
| | |
|---|---|
| *A61B 5/00* | (2006.01) |
| *A61B 5/11* | (2006.01) |
| *G06F 19/00* | (2018.01) |
| *G16H 40/67* | (2018.01) |

(52) U.S. Cl.
CPC .......... *A61B 5/4082* (2013.01); *A61B 5/0022* (2013.01); *A61B 5/1101* (2013.01); *A61B 5/1125* (2013.01); *A61B 5/4842* (2013.01); *G06F 19/00* (2013.01); *G16H 40/67* (2018.01)

(58) Field of Classification Search
CPC ...... A61B 5/11–5/1128; A61B 5/4076–5/4094
See application file for complete search history.

(56) References Cited

U.S. PATENT DOCUMENTS

| | | | | |
|---|---|---|---|---|
| 5,562,104 | A * | 10/1996 | Hochberg | A61B 5/16 600/595 |
| 6,311,042 | B1 * | 10/2001 | DeSchrijver | G06F 3/03545 340/5.52 |
| 6,517,480 | B1 * | 2/2003 | Krass | A61B 5/16 600/300 |
| 8,702,629 | B2 | 4/2014 | Giuffrida et al. | |
| 8,950,864 | B1 * | 2/2015 | Massengill | A61B 5/4064 351/209 |

(Continued)

OTHER PUBLICATIONS

"Wearable and wireless accelerometer systems for monitoring Parkinson's disease patients—A perspective review", Advances in Parkinson's Disease, vol. 2, No. 4. 113-115 (2013), Robert LeMoyne.

(Continued)

*Primary Examiner* — Max Hindenburg
(74) *Attorney, Agent, or Firm* — Robert M. Schwartz; Kerry P. Sisselman (57) ABSTRACT

An integrated device that detects and stores, in digital form, the muscle movements that occur when an operator traces a defined figure or pattern with a pointing device, such as a laser beam. The movement data is stored and analyzed for monitoring and diagnosing a neuromuscular condition or neuromuscular variations. Movement disorders can be determined and progression and change analyzed over time using the stored data.

20 Claims, 4 Drawing Sheets

(56) References Cited

U.S. PATENT DOCUMENTS

| | | | | |
|---|---|---|---|---|
| 2010/0156785 A1* | 6/2010 | Nakaoka | ............... | G06F 3/0346 345/157 |
| 2014/0074180 A1* | 3/2014 | Heldman | ............ | A61B 5/1101 607/45 |
| 2014/0100486 A1* | 4/2014 | Alberts | ................ | A61B 5/1106 600/595 |
| 2014/0113258 A1* | 4/2014 | DeGoede | ................. | A61B 5/11 434/155 |
| 2014/0168176 A1* | 6/2014 | Nowatzyk | ........... | G06F 3/03545 345/179 |

OTHER PUBLICATIONS

"Wireless accelerometer configuration for monitoring Parkinson's disease hand tremor"—Advances in parkinson's Disease, vol. 2. No. 2. 62-67 (2013), Robert LeMoyne, Timothy Mastroianni and Warren Grundfest.

Smartphone-based Evaluation of Movement Disorders: Quantitative Measurements vs Clinical Assessment Scores, IEEE Conference in Engineering in Medicine and Biology, 2014,N. Kostikis, D. Hristu-Varsakelis, M. Arnaoutoglou and C. Kotsavasiloglou.

www.imedicalapps.com/2011/02/iphone-accelerometer-diagnose-parkinsons-disease.

http://mobilhealthnews.com/13812/wireless-sensors-tablet-computer-mesaure-parkinson.

\* cited by examiner

FIG. 5F ns in neuromuscular control when tracing a defined pattern and, more particularly, relates to a device, system and method useful to standardize measure and analyze neuromuscular interactions and activity that occurs when a subject is required to trace a prescribed target pathway.

Description of the Related Art

Numerous neuromuscular problems and disorders affect the ability of the brain to transmit the appropriate signals to the muscles. Injury, stroke, Parkinson's, Huntington's, Tourette syndrome, drugs, and even fatigue are but a few examples. Tremors are involuntary muscle contractions that oscillate in frequency. Hypokinesia is a hesitation or decrease in muscle movement usually associated with damage to the basal ganglia. Hyperkinesia is an increase in muscle movements that results in excessive normal or abnormal movements. Such movements are variously described as dystonia, chorea, athetosis, myoclonus, tremors and tics. Measurements of neuromuscular movement are often very subjective and rarely done with the accuracy required for creating large consistent databases. This is especially true for comparison of random muscle movements and aberrant muscle movements occurring during conscious activities such as eating and trying to use a cell phone. Good measurement instrumentation is usually found at sites that require the patient to travel some distance to be properly tested. Other devices are expensive and may require a doctor's recommendation.

However, many modern devices, such as smartphones, already incorporate a computer linked to a highly accurate clock, an accelerometer and a gyroscope. These parts are all necessary to measure muscle movements, but currently cannot be used for measuring neuromuscular actions diagnostically without being associated with a means to standardize and store repeated movements over time, over distances, and between normal and abnormal conditions.

Additionally, many modern devices, such as smartphones, incorporate wireless communication capabilities that enable the digital storage of vast amounts of data secondary to the device. For example, data from a modern device may be stored wirelessly in "cloud" storage (e.g. "the cloud"). Once neuromuscular actions can be recorded and transmitted in a consistent and reproducible way, and then the necessary databases can be established to develop diagnostic algorithms discriminating various neuromuscular conditions.

There are currently no devices available that enable neuromuscular movement measurement, data processing, transmission, storage, and large database analysis during conscious directed activities such as drawing a standard figure eight. There are currently no devices or applications available that enable the inexpensive and wide spread use for monitoring and prognosticating neuromuscular variations associated with the measurement of functional performance relative to target patterns.

U.S. Pat. No. 8,679,038 to Giuffrida discloses a movement disorder monitor that is worn continuously to provide continuous information to measure the severity of a subject's movement disorder. See also, for example, U.S. Patent Application Publication No. 2015/0073310 to Pracar. What is needed is a device and system that need not be used continuously, but can provide vast amount of data over time, to diagnose a neuromuscular variations.

U.S. Pat. No. 7,312,863 discloses a motion-compensating light-emitting apparatus wherein a light-emitting apparatus, for enabling a spot of light to be projected on a desired target located a distance away such that the spot is projectable on the desired target without any or substantially any undesired movement. What is needed is a device and system that detects movement, but does not compensate for it, but rather, stores and/or analyzes the data illustrating the undesired movement for determining neuromuscular variation while using the light-emitting apparatus to trace a predetermined pattern.

Additionally, smartphones, such as the IPHONE® have been used, in general, for the quantification of Parkinson's disease hand tremor wherein the IPHONE® was mounted in a glove worn by the patient. See, for example, Robert LeMoyne, "Wearable and wireless accelerometer systems for monitoring Parkinson's disease patients—A perspective review", SciRes, Vol. 2, No. 4, 113-115 (2013). What is further needed is a convenient, inexpensive and consistent device for measuring neuromuscular actions, not merely while wearing a sensor, but rather, relative to one or more easily available standardized patterns traced by the user and a system for permitting analysis of the results over time.

BRIEF SUMMARY OF THE INVENTION

It is accordingly an object of the invention to provide a device, system and method to standardize, measure, and analyze the neuromuscular interactions and activity that occurs when a subject is required to trace a prescribed target pathway. According to one embodiment, a convenient, inexpensive, consistent and reproducible measurement of neuromuscular actions over time is obtained using a pointing device interfaced with new or existing technology having highly accurate clock(s), gyroscope(s), and/or accelerometer(s) to permit tracing of an easily available standardized pattern or set of patterns. The measurement data obtained from such devices during the performance of pattern tracing is then used to determine variations in neuromuscular control.

In one embodiment, a computing device capable of measuring three dimensional movements along the x, y and z axes, acceleration and time is coordinated with a pointing device. The computing device of the present embodiment includes computer processing, memory storage and wireless data transmission capabilities, can perform highly accurate time measurements, and incorporates at least one of a gyroscope, gravimeter and/or an accelerometer. The device can additionally be interconnected with a communications network, such as the Internet, and cloud storage. One particular device that can be used as the computing device of the present embodiment is a smartphone. The computing device is programmed by software stored in memory of the computing device and executed by a processor of the computing device, to measure, analyze, store and transmit the movement, acceleration and time detected and/or calculated by the computing device while the subject traces a prescribed target. In one embodiment, the target is constructed and selected based on the analysis of data and information obtained in the system during the performance on like targets by normal individuals and patients with neuromuscular abnormalities. Targets are optimized based on optimal differentiation of normal individual and patient performances.

In one embodiment of the invention, an integrated device detects and stores, in digital form, the muscle movements that occur when the operator of the device traces a defined figure using the pointing device. The movement data is stored in a system database, which is used to perform algorithmic analysis for the purpose of patient monitoring and diagnostics. Movement disorders associated with neuromuscular communication can be determined using the stored data, and any progression and/or change analyzed over time.

The use of this invention with prescribed targets enables the widespread storage and analysis of subject data via the Internet and cloud-based storage. Additionally, cloud-based storage permits the performance of general and algorithmic analyses necessary for prognostication of neuromuscular movement changes associated with disease, injury, chemical and fatigue effects.

In one embodiment of this invention neuromuscular cognitive activity can be analyzed in a gaming mode associated with the target tracing of mazes or problem solving tracings.

In another embodiment of the invention optimal neuromuscular cognitive activity in association with algorithmic analysis is used for mind body training and gaming rather than diagnostically.

Although the invention is illustrated and described herein as an integrated device to measure variations in neuromuscular control when tracing defined target patterns, and a system and method of using the integrated device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

For the purpose of illustrating the invention, there is shown in the drawings an exemplary embodiment that is presently preferred, it being understood however, that the invention is not limited to the specific methods and instrumentalities disclosed. Additionally, like reference numerals represent like items throughout the drawings. In the drawings.

DETAILED DESCRIPTION OF THE INVENTION

The present invention uses a movement sensing device, integrated with a pointing device, to enable the non-subjective measurement of movement for the purpose of detecting, monitoring, and storing variations in muscle neuron interactions that occur during the visual sensory tracing of defined figures.

Referring now to FIGS. 1-3A, there is illustrated one particular system 100 of the present invention. More particularly, an integrated device 110 is provided that includes a computing device 112 attached to/integrated with a pointing device 114. The computing device 112 includes a processor 160 and internal memory 161 and is configured to execute instructions (such as is in software or firmware stored in non-transitory memory 161 of the device 112) to perform a method in accordance with the invention. In one particular embodiment, the computing device 112 is responsible for the measurement, storage and comparison of each individual subject's brain-to-muscle motor control variation when tracing one or more defined tracing patterns using the attached/integrated pointing device 114. Additionally, if desired, the computing device 112 also includes a touch sensitive or interactive display 165 for providing feedback to and receiving feedback from the user, and a communications device 163 for communicating data to a remote location. Most preferably, the computing device 112 is a commonly found device already in the possession of a user 115, such as a smartphone or other intelligent device.

Figure 1:
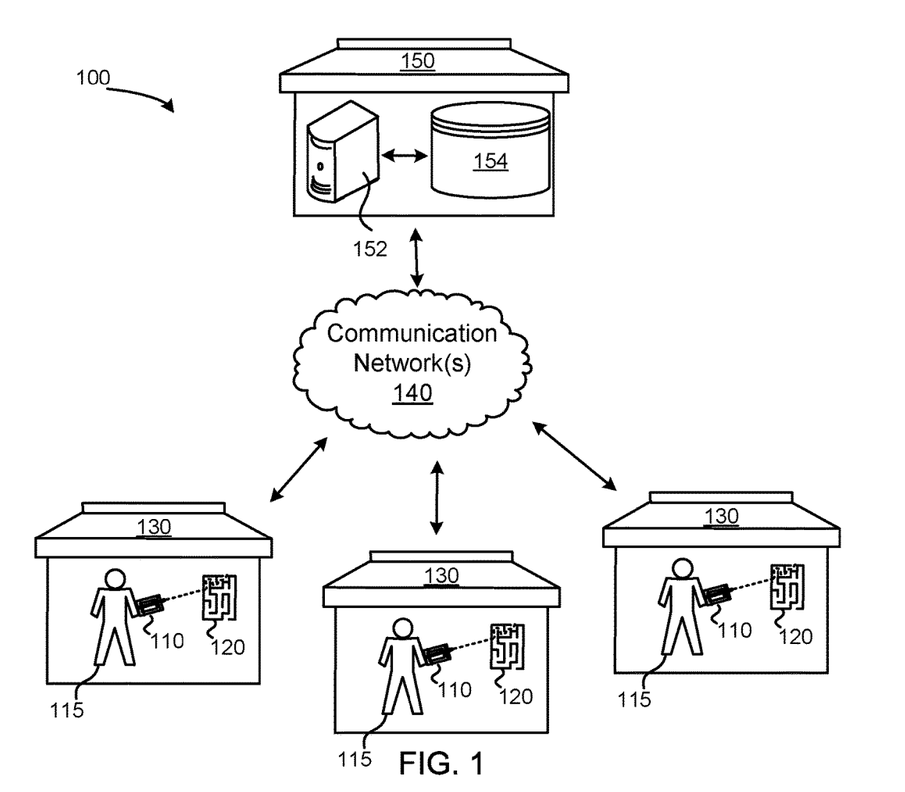
FIG. 1 is a simplified illustration of a system in accordance with one particular embodiment of the invention.
Figure 2:
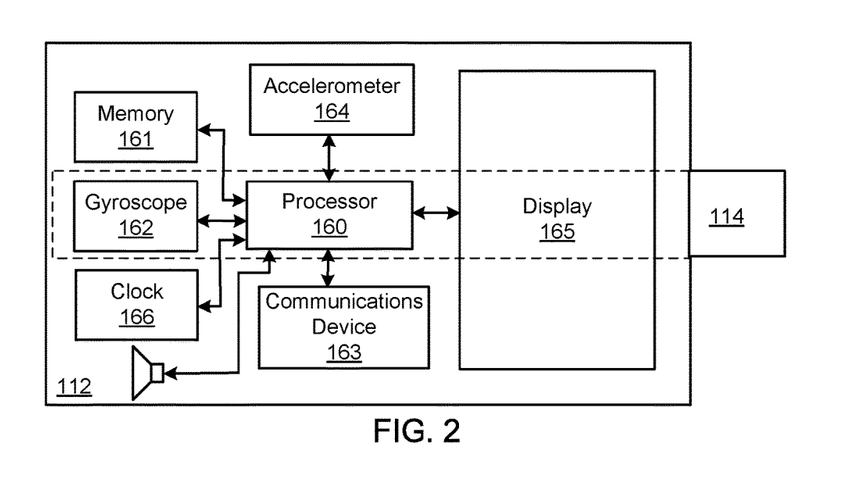
FIG. 2 is a simplified block diagram of an integrated device that includes a secondary x, y, z movement, acceleration detection, storage and transmitting computing device, in accordance with one particular embodiment of the invention.

Such a computing device 112 advantageously includes circuitry and sensors that can detect changes in the x, y, z directions (i.e., a gyroscope 162), acceleration (i.e., accelerometer 164), and time (i.e., clock 166) during the tracing of a specified target pattern 120. In particular, the system 100 embodies the ability to utilize readily available devices that incorporate accelerometers, gyroscopes and highly accurate timing. Note that the exemplary use of the gyroscope 162, accelerometer 164 and clock 166 is not meant to limit the invention only to these devices. Rather, the device 112 could instead, or in addition to, use other motion sensing, position sensing and/or timing devices, such as, gravitometers, magnetometers, resistance bend sensors, GPS (global positioning system), multilateration of radio signals from towers, laser positioning or radar positioning for the measurement of movement when performing a standardized task using a pointing device, without departing from the scope and spirit of the present invention.

Movement data collected by the device 112 can be stored, digitally, and used to calculate comparisons and measure changes in the performance of neuromuscular performance for individual subjects 115 over time. The stored data of subjects can be compared with normal patterns and results, and also, with patterns known to be associated with neurological, muscular and functional abnormalities. In one particular embodiment of the invention, the results data can be generated, analyzed and stored locally to the user 115, at the user's location 130 and/or in non-transitory memory of the computing device 112. Alternately, or in addition to such local storage, the results data can be communicated from the computing device 112 to a remote location 150, via one or more communications networks 140, for analysis by a remote server 152 and/or storage in one or more remote databases 154.

In one particular embodiment of the invention, data from multiple individuals 115 are transmitted to one or more remote databases in order to accumulate and store a large database of subject performance that is comparable and analyzable via the performance of the standardization of the pointing task. In this embodiment, the database is constructed via the Internet cloud storage transmission of movement data, which in turn enables the comparison of normal and other than normal performances in order to develop processing algorithms that are utilized for characterization of movement patterns with defined neuromuscular conditions. Diagnostic reliability emerges from the analysis of the large database made available via the use of this readily affordable and available device 110 in a system 100.

The basic device 110 may be described, in its most simple and general form, as a laser pointer or other narrow-beamed light pointing device 114 attached to a smartphone 112 programmed with a specialized application for collecting, storing, analyzing and/or communicating position and timing data. In one embodiment, the device 110 communicates data collected by the device 110 to a cloud server 152 and/or remote database 154 over a communications network 140, such as the Internet. For example, the device 112 records the detected x, y, z movements and acceleration of the device 112 over time when a subject traces a selected FIG. 120 from a predefined distance. The invention enables the general public anywhere in the world to be voluntarily, remotely and inexpensively monitored in association with neuromuscular disease detection, disease progression and effective changes that may be associated with clinical drug trials. Application for Huntington's Disease, Alzheimer's Disease, and Parkinson's Disease are of primary importance.

Referring now to FIGS. 1-4D, in one particular embodiment of the invention, the laser pointer or other non-coherent light pointing device 114 is attached to, or integral with, the computing device 112, which measures and records muscle or other body movements and acceleration in the three dimensional (x, y, z) axis over time when the user 115 traces a predefined FIG. 120, 125 at various predefined distances. More particularly, the computing device 112 is configured to record movement data of the pointing device 114 (and by its attachment to of the computing device 112, movement data of the integrated device 110) relative to a particular pattern 120 or 125 predefined in the computing device 112.

Data collected by the device 110 can be analyzed locally and/or transmitted (by the communications device 163 and one or more communications networks 140) to a remote location 150 for remote storage and analysis of individualized data, instantaneously and/or over time. For example, data relating to muscle or other movement and acceleration in the three dimensional (x, y, z) axis over time for a subject 115 tracing a predetermined FIG. 125, with a laser beam 114b emitted from an aperture and lens set 114a, at one or various distances, can be sent from the device 110 to a remote server that analyzes the data for that test instance, and also stores it for later comparison with future data generated by the subject 115. The collected data can be used for the diagnosis of neurological disorders through algorithmic analysis of the data. Note that, the advantages of the present invention can be achieved even without requiring cloud processing or cloud storage. For example, if desired, the data can additionally, or alternately, be stored locally on the device 110 (in a non-transitory memory 161 of the computing device 112) for analysis of the data of the individual 115 using the particular device 110, over time.

When analysis and storage are performed via cloud computing, as illustrated more particularly in FIG. 1, personalized data of an individual subject is used for the unique identification of individuals from all other users in the database 154, and can be used for the identification of individual performance changes due to effect of drugs, fatigue, muscle deterioration, or neurological deterioration, for example. Additionally, analysis of the collected data for an individual can be used for the development and application of algorithms that are used for personal identification, the effect of drug, fatigue or other environmental influences, muscle deterioration, neurological or other cellular deterioration or change.

In one particular embodiment, data collected while tracing a predetermined FIG. 125 at various distances with a laser or non-coherent light pointing device 114 attached to or integral to a computing device 112 measuring and/or recording muscle or other movement and acceleration in the three dimensional (x, y, z) axis over time, can be used for following individualized patients during drug trials. Additionally, if desired, the collected data can be used for a creating a cloud storage database 164 for applications in determination of diagnostic parameters and algorithms associated with early disease detection, following disease progression, and following other neuromuscular changes.

In one particular embodiment of the invention, if desired, the device 110 is attached to a hand, arm or wrist of a user 115 using one or more of: elastic, hook and loop fasteners, a band, etc., so that a user is able to isolate separate muscle groups when tracing said figure. Additionally, in one embodiment, the pointing device 114 is attached to the computing device 112 with at least one of: (a) a plastic, metal or cloth case that holds the device 112 and incorporates a section of the case which allows the insertion or attachment of a laser pointer 114; (b) a holder or clip for a laser pointer 114 that can be attached to a device 112 via an elastic, mechanical spring, hook and loop fastener, such as VELCRO®, or adhesive interaction; (c) a glove in which the device 112 and pointing device 114 can be attached or inserted or (d) a pistol type grip into which the device 112 and pointing device 114 are attached or inserted. In a further embodiment illustrated more particularly in FIG. 4D, the pointing device 114 can be made to extend naturally from one end of the device 112, for example, by insertion (in the direction of the arrow "a") of a pin 114d of the pointing device 114 into an earphone or mic jack of the device 112. As with the laser pointers 114 of FIGS. 1-4C, the device 114 of FIG. 4D can be a completely encapsulated laser pointing device 114, having a laser aperture and lens set 114a, through which the coherent light 114b is emitted, an on-off switch 114c and a battery (not illustrated). In a further embodiment, the use of a physical pointing structure, such as a long lightweight pole, may be substituted for the described laser or non-coherent light source 114 attached to the computing device 112.

Referring now to FIGS. 1-5F, the types of patterns 120, 125 to be traced can include, as appropriate, a spot, line, circle or other plain or complex figure. The pattern 120, 125 selected is first input into the computing device 112, prior to beginning a tracing. Alternately, the type of the pattern 120, 125 to be traced can be determined by the computing device 112, by comparison with stored movement patterns associated with the standardized patterns.

For example, FIGS. 5A-5F illustrates certain possible pointing device targets for use with an integrated device 110, such as that illustrated in connection with FIGS. 1-3B. The target pattern or diagram 120, 125 is a vital part of the invention for measuring variations in neuromuscular control for the detection and prognostication of neuromuscular variations and abnormalities.

Figures 4A, 4B:
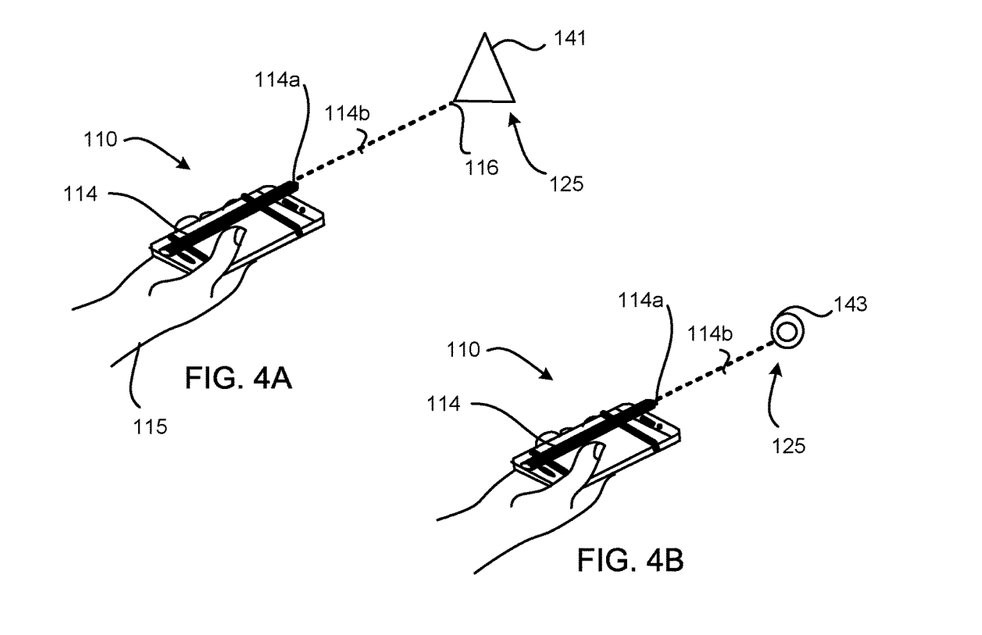
FIGS. 4A-4C are exemplary illustrations of one particular embodiment of the invention, wherein a laser pointer is attached to a computing device with straps or elastic bands and the device is held in the hand and moved to trace a target, as depicted.
Figures 4C, 4D:
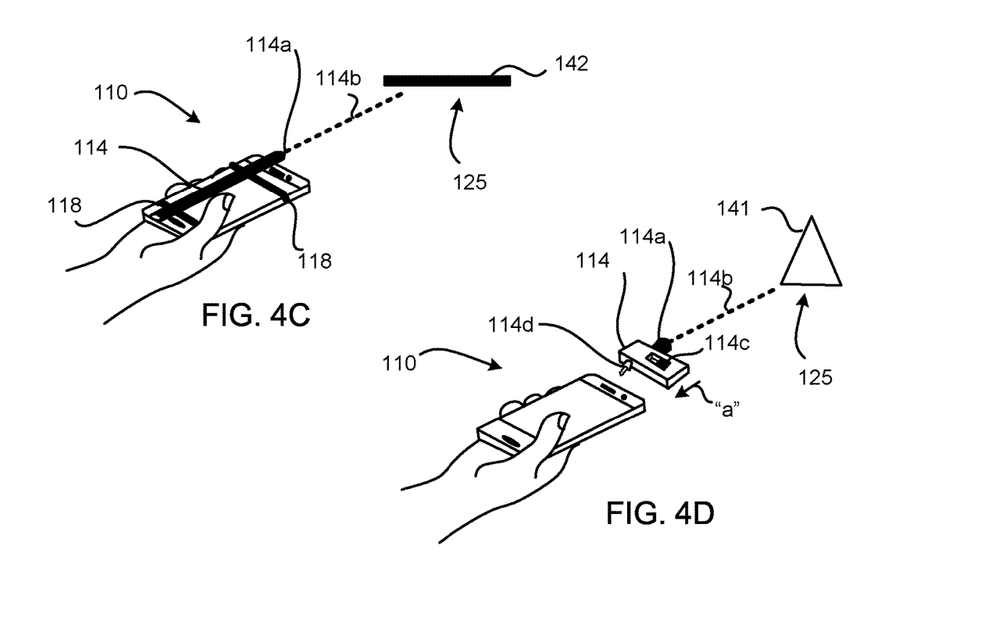
FIG. 4D is a partially exploded view of one example of another particular embodiment of the invention, wherein a laser pointer is attached to a computing device held in the hand and moved to trace a target, as depicted.
Figure 5A:
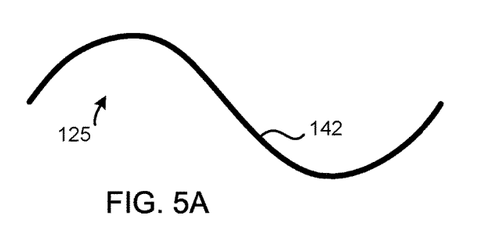
FIGS. 5A-5F illustrate exemplary diagrams representing possible pointing device targets for use with a device and system of the present invention.
Figure 5B:
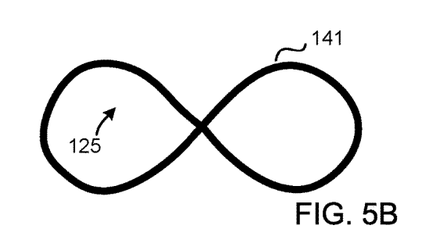
Figure 5C:
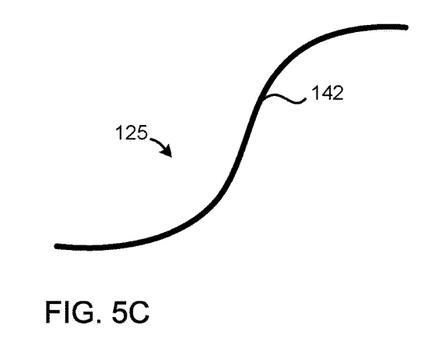
Figure 5D:
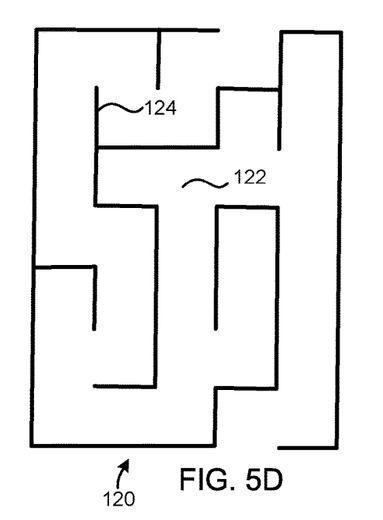
Figure 5E:
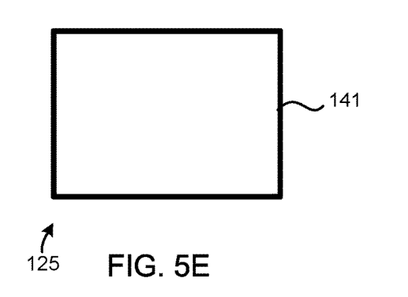
Figure 5F:
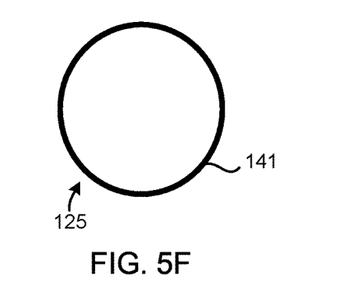

Additionally, the patterns 120, 125 illustrated in FIGS. 5A-5F are selected to optimize the detection of neuromuscular movements and enhance detection and analysis of neuromuscular abnormalities. The set of patterns used is additionally selected for the optimization of the normalization, standardization of control parameters necessary for calibration and algorithmic development. The subject 115 will be asked to interact with the selected pattern in predetermined ways. For example, referring now to FIG. 4A-5F, the subject 115 may be asked to trace the outline 141 of a simple geometric shape 125 (FIGS. 4A, 4D, 5B, 5E, 5F), or trace a line 142 (FIGS. 4C, 5A, 5C) with the beam end 116 (i.e., visualized as a spot on the target) of the integrated device 110. In one embodiment, the subject may be asked to trace inner and/or outer circles of concentric circles 143, or a space between two concentric circles, as illustrated in FIG. 4B. In a further embodiment, a pattern may be provided in the form of a maze 120, which requires the subject to make conscious logic based decisions in association with neuromuscular movements in a gaming format. Other types of patterns may be produced that make the testing more game-like, and which test decision making in association with neuromuscular movements.

A pattern or set of patterns are provided to the user 115 for use in the system 100. As discussed above, FIGS. 5A-5F illustrate various exemplary types of patterns or targets 120, 125, though other patterns and targets may be used without departing from the scope and spirit of the present invention. In one embodiment, one or more patterns 120, 125 are provided electronically for printing out by the user 115 or as paper copies to the user 115. A paper version of the pattern 120, 125 can then be secured to a wall with tape or other light adhesive, magnets, pins or tacks. In another embodiment, one or more patterns 120, 125 are provided on an external display of the user 115, such as on a laptop or desktop computer screen, a television display or another type of electronic display. The one or more patterns are preferably a set of patterns provided to the user. Additionally, it is important to understand that the one or more patterns are traced external to the integrated device 110. Note that the integrated device 110 does not physically touch the pattern, but only the beam end 116 of the laser or light beam intersects with the pattern 120, 125.

Referring to FIGS. 1-4D, a method of using an integrated device 110, in accordance with one embodiment of the invention, will now be described. The integrated device 110 is held in, or secured to, a user's hand 115a, and includes a light pointing device 114 that transmits a beam of light 114b towards a predetermined figure or target 120, 125. In one embodiment, the pointing device 114 is attached to a computing device 112, such as a smartphone or other intelligent device, with one or more attachment bands 118, or a pin 114d. This is not meant to be limiting, as other ways of securing the pointing device 114 to the computing device 112, or of integrating the pointing device 114 with the computing device 112, can be used without departing from the scope and spirit of the present invention.

A particular pattern 120 or 125 is selected, either by the subject or, in one embodiment, through guidance from a software application ("app") executing on the computing device 112 and displayed on a wall or screen visible to the subject 115. For example, the type of pattern to be traced or used (i.e., spot, line, circle, or plain or complex figure) is input into the computing device, preferably by selection from a menu of the app or using image capture with a camera of the computing device. Alternately, the type of pattern can be determined by the app executing on the computing device 112 by comparison with stored movement patterns associated with the standardized patterns. Prior to the initiation of testing, the subject 115 is instructed to stand or sit a predefined distance from the pattern 120, 125 for the entire testing. The integrated device 110 is pointed towards the target 120, 125 by the user 115, in order to perform an exercise which can be measured and evaluated.

Testing is initiated and monitored by the software app executing on the computing device 112. In one embodiment, the recording, processing and storage of x, y, z movement, accelerations, and time is initiated in the computing device 112 by an audible timing alarm, such as a buzzer, or by an audible command or tone such as saying the word "start". Alternately, if desired, the recording, processing and storage of x, y, z movement, accelerations, and time can be initiated in the computing device 112 by a specific set of x, y, z and acceleration movements, such as by shaking the device up and down. In another embodiment, the recording, processing and storage of x, y, z movement, accelerations, and time is initiated in the computing device 112 by another device, such as a button wirelessly connected to the computing device 112 via a wireless protocol, such as Bluetooth®. Other ways of starting the test may be used, however. For example, the app executing on the computing device 112, once started, can provide instructions to a user 115 on the display 165 of the computing device 112 or, more preferably, can provide spoken instructions to the user 115 to walk the user through the testing process.

During use, the subject 115 moves their hand 115a to aim and point the integrated device 110 towards a target 120, 125, so that the beam of light 114b projects onto the target 120, 125. The user 115 then, as instructed, will move the integrated device 110 and projected beam of light 114b relative to the target 120, 125. As an example, the user 115 will trace the projected beam of light 114b having a beam end 116, against the target 125 or through the interlinear spaces of a maze 120, so that movements by the user 115 can be calculated against a known and predicted movement, to detect variations of the user's movements. For example, if the subject 115 is tracing the triangle pattern 125 illustrated in FIG. 4A, the movement of the device 110 during the tracing operation is compared to ideal, known or predicted movement for tracing the triangle pattern 125, to determine variations in the neuromuscular control of the subject 115. Although the comparison can be performed locally by the computing device 112, in one particular embodiment of the invention, the movement data is collected by the computing device 112, and this movement data and other reference data calculated or measured within the device 112 are transmitted by the computing device 112 to a remote collection site 150, for analysis. As discussed hereinabove, remote collection site 150 may be a cloud computing site.

Figure 3A:
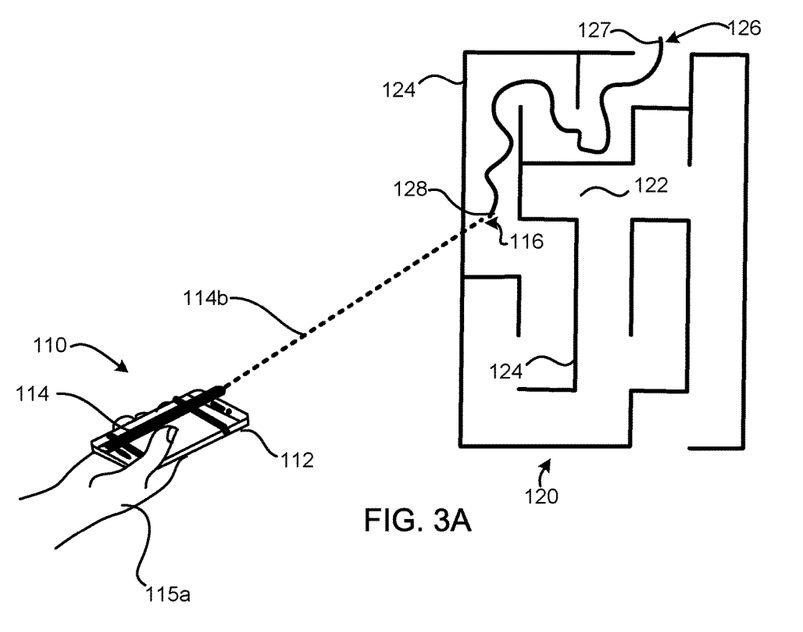
FIGS. 3A and 3B are simplified illustrations of a user holding an integrated device in accordance with one particular embodiment of the invention, with the beam of light projected on a target and showing the path of the beam of light
Figure 3B:
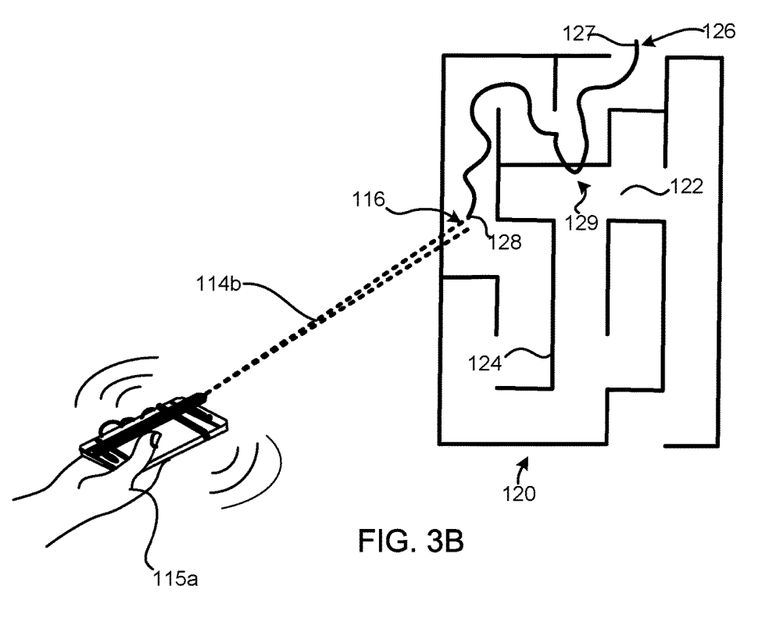

In the particular example illustrated in FIG. 3A, the target selected is a maze 120. The subject 115 is instructed to stand a predetermined distance from the displayed maze 120 and point the integrated device 110 at the maze 120. The user 115 guides the device 110, and correspondingly the beam end 116 through the interlinear spaces 122 between the lines 124 of the maze 120. This is illustrated by the target line 126, which starts at line beginning 127 and is in progression at line point 128. This target line 126 represents the line followed by the beam end 116 of the integrated device 110 held in and manipulated by a user's hand 115a. The path of target line 126 can be used to record and measure the user's motions, including but not limited to at least detecting when the beam end 116 is within the preferred target area 122 or when the beam end 116 touches or crosses over a line 124 of the maze 120 (see, for example, 129 in FIG. 3B).

Referring back to FIGS. 1-3B, the present invention is useful in diagnosing and/or tracking the progression of a disease or syndrome having neuromuscular components. For example, a user 115 can perform a test, such as solving a maze 120, as illustrated in FIG. 3A. The results of the test can be processed and stored in a local or cloud database 154. In addition to storage, the results can be analyzed and/or compared with other test results, including ideal test results and/or test results of other users having identified conditions, stored in the database 154 to find patterns indicative of a neuromuscular condition or disorder.

Additionally, test results can be analyzed to determine a progression of a neuromuscular condition. For example, the results for the test performed in FIG. 3A can be stored and used as a baseline for comparison to later obtained results for the same pattern. For example, referring now to FIGS. 1, 3A and 3B, results from a test performed by a user 115 on the maze 120 can be saved and used as a baseline for comparison with later performed tests to determine a progression of a neuromuscular condition. For example, by comparing the results obtained in FIG. 3B with the previously stored results obtained in connection with FIG. 3A to determine a degree to which a neuromuscular tremor has worsened. The results of such a comparison can be stored, with the test results, and used by physicians to evaluate treatment options.

Thus, the present invention utilizes an integrated device that detects and stores, in digital form, the muscle movements that occur when the operator traces a defined figure using a pointing device such as a laser beam. The movement data is stored and then used to create the data base necessary to enable algorithmic analysis for the purpose of monitoring and diagnostics. Movement disorders associated with neuromuscular communication can be determined and progression and change analyzed over time in association with the stored data. A system and method for using the device are additionally provided. The present invention provides the capability for an inexpensive (because the user 115 may already own a smartphone or other intelligent device) and widespread measurement, analysis, transmission and storage of neuromuscular activity associated with performing a standardized task.

Accordingly, while a preferred embodiment of the present invention is shown and described herein, it will be understood that the invention may be embodied otherwise than as herein specifically illustrated or described, and that within the embodiments certain changes in the detail and construction, as well as the arrangement of the parts, may be made without departing from the principles of the present invention as defined by the appended claims.

The invention claimed is:

1. A device for measuring variations in neuromuscular control of a user, comprising:
an integrated device, including:
a computing device configured to be held by the user;
a pointing device attached to, or integrated with the computing device, the pointing device including an end portion;
the computing device configured to detect three-dimensional movement data of the integrated device relative to a particular pattern predefined in the computing device while the user is tracing the pattern;
wherein the pointing device is configured for the end portion to be pointed at said pattern at a predefined distance from said pattern to trace said pattern, without the end portion physically touching the pattern.

2. The device of claim 1, wherein the computing device includes a motion sensor and timing circuitry.

3. The device of claim 2, wherein the motion sensor measures acceleration in the x, y and z axes.

4. The device of claim 2, wherein the computing device is a smartphone.

5. The device of claim 1, wherein the pointing device is a laser pointing device.

6. The device of claim 1, wherein the computing device is further configured to compare the detected movement data to known movement data for the particular pattern.

7. The device of claim 1, wherein the computing device is further configured to transmit the detected movement data to a remote computer for storage in a remote database.

8. The device of claim 7, wherein the remote computer is a cloud computer and the data is transmitted over the Internet.

9. The device of claim 8, wherein the remote computer compares the detected movement data over time, to determine a progression of a neuromuscular variation of the user.

10. The device of claim 7, wherein the remote computer is configured to compare the detected movement data to known movement data for the particular pattern.

11. The device of claim 7, wherein the remote computer is configured to compare the detected movement data to movement data of other users stored in the database for the particular pattern.

12. A system for measuring variations in neuromuscular control of a user, comprising:
a device according to claim 1;
at least one pattern to be traced by the user.

13. The system of claim 12, wherein the at least one pattern is a set of patterns.

14. The system of claim 12, wherein the pattern is at least one of a line, a simple figure and a complex figure.

15. The system of claim 14, wherein the pattern is a maze, and tracing is performed by the user in the interlineal spaces of the maze.

16. A method for measuring variations in neuromuscular control of a user, the method comprising the steps of:
providing an integrated device including a computing device configured to be held by the user and a pointing device attached to, or integrated with the computing device, the computing device configured to detect movement data of the integrated device relative to a particular pattern predefined in the computing device;
pointing the pointing device at a pattern external to the integrated device at a predefined distance from said pattern and tracing the pattern with an end portion of the pointing device without the end portion physically touching the pattern;

measuring movement data of the user in three dimensions while the user is tracing the pattern; and analyzing the movement data to determine differences between the movement data of the user and of stored movement data for the particular pattern.

17. The method of claim 16, wherein the pattern is a set of patterns provided to the user.

18. The method of claim 16, wherein the pointing device is a laser pointer and the computing device is a smartphone.

19. The method of claim 16, the analyzing step is performed by the computing device.

20. The method of claim 16, wherein the computing device transmits the measured movement data to a remote computer and the analyzing step is performed by the remote computer.

\* \* \* \* \*